US012746239B2

(12) United States Patent
Clines

(10) Patent No.: US 12,746,239 B2
(45) Date of Patent: Sep. 29, 2026

(54) COMPOSITIONS AND METHODS COMPRISING ENDOTHELIN A RECEPTOR ANTAGONISTS AND ANDROGEN THERAPIES

(71) Applicant: United States Government As Represented By The Department of Veterans Affairs, Washington, DC (US)

(72) Inventor: Gregory A. Clines, Ann Arbor, MI (US)

(73) Assignee: United States Government As Represented By The Department of Veterans Affairs, Washington, DC (US)

( * ) Notice: Subject to any disclaimer, the term of this patent is extended or adjusted under 35 U.S.C. 154(b) by 255 days.

(21) Appl. No.: 17/614,956

(22) PCT Filed: May 29, 2020

(86) PCT No.: PCT/US2020/035042

§ 371 (c)(1),
(2) Date: Nov. 29, 2021

(87) PCT Pub. No.: WO2020/243378

PCT Pub. Date: Dec. 3, 2020

(65) Prior Publication Data

US 2022/0218701 A1 Jul. 14, 2022

Related U.S. Application Data

(60) Provisional application No. 62/855,105, filed on May 31, 2019.

(51) Int. Cl.

| | |
|---|---|
| ***A61K 31/497*** | (2006.01) |
| ***A61K 31/4025*** | (2006.01) |
| ***A61K 31/415*** | (2006.01) |
| ***A61K 31/4166*** | (2006.01) |
| ***A61K 31/4439*** | (2006.01) |
| ***A61K 31/58*** | (2006.01) |
| ***A61K 45/06*** | (2006.01) |
| ***A61P 13/08*** | (2006.01) |
| ***A61P 35/04*** | (2006.01) |

(52) U.S. Cl.
CPC ........ *A61K 31/497* (2013.01); *A61K 31/4025* (2013.01); *A61K 31/415* (2013.01); *A61K 31/4166* (2013.01); *A61K 31/4439* (2013.01); *A61K 31/58* (2013.01); *A61K 45/06* (2013.01); *A61P 13/08* (2018.01); *A61P 35/04* (2018.01)

(58) Field of Classification Search
CPC .............. A61K 31/497; A61K 31/4025; A61K 31/415; A61K 31/4166; A61K 31/4439; A61K 31/58; A61K 45/06; A61P 13/08; A61P 35/00; A61P 35/04
See application file for complete search history.

(56) References Cited

U.S. PATENT DOCUMENTS

2009/0130118 A1 5/2009 Cohen

FOREIGN PATENT DOCUMENTS

WO WO 2016/081603 5/2016
WO PCT/US2020/035042 5/2020

OTHER PUBLICATIONS

Dale R Shepard & Robert Dreicer (2010) Zibotentan for the treatment of castrate-resistant prostate cancer, Expert Opinion on Investigational Drugs, 19:7, 899-908, DOI: 10.1517/13543784.2010.49182 (Year: 2010).*
Smith MR et al. Apalutamide Treatment and Metastasis-free Survival in Prostate Cancer. N Engl J Med. Apr. 12, 2018;378(15):1408-1418. doi: 10.1056/NEJMoa1715546. Epub Feb. 8, 2018. PMID: 29420164. (Year: 2018).*
Bubendorf L, Schopfer A, Wagner U, et al. Metastatic patterns of prostate cancer: an autopsy study of 1,589 patients. *Hum Pathol.* 2000;31(5):578-583.
Weilbaecher KN, Guise TA, McCauley LK. Cancer to bone: a fatal attraction. *Nat Rev Cancer.* 2011;11(6):411-425.
Nelson JB, Hedican SP, George DJ, et al. Identification of endothelin-1 in the pathophysiology of metastatic adenocarcinoma of the prostate. *Nature Medicine.* 1995;1(9):944-949.
Yanagisawa M, Kurihara H, Kimura S, et al. A novel potent vasoconstrictor peptide produced by vascular endothelial cells. *Nature.* 1988;332(6163):411-415.
Nelson JB, Nabulsi AA, Vogelzang NJ, et al. Suppression of prostate cancer induced bone remodeling by the endothelin receptor A antagonist atrasentan. *Journal of Urology.* 2003;169(3):1143-1149.
Yin JJ, Mohammad KS, Kakonen SM, et al. A causal role for endothelin-1 in the pathogenesis of osteoblastic bone metastases. *Proceedings of the National Academy of Sciences of the United States of America.* 2003;100(19):10954-10959.
Clines GA, Mohammad KS, Bao Y, et al. Dickkopf homolog 1 mediates endothelin-1-stimulated new bone formation. *Molecular Endocrinology.* 2007;22:486-498.
Little RD, Carulli JP, Del Mastro RG, et al. A mutation in the LDL receptor-related protein 5 gene results in the autosomal dominant high-bone-mass trait. *American Journal of Human Genetics.* 2002;70(1):11-19.

(Continued)

*Primary Examiner* — Bruck Kifle
*Assistant Examiner* — Kevin S Martin
(74) *Attorney, Agent, or Firm* — BALLARD SPAHR LLP

(57) ABSTRACT

Disclosed are compositions comprising an endothelin A receptor ($ET_AR$) antagonist, an anti-androgen therapy, and chemical castration therapy. Also disclosed are compositions comprising an $ET_AR$ antagonist, copackaged or coformulated with an anti-androgen therapy. Disclosed are methods of preventing prostate cancer metastasis comprising administering to a subject having prostate cancer an $ET_AR$ antagonist, an anti-androgen therapy, and castration therapy. Also disclosed are methods of increasing survival in a prostate cancer patient, comprising administering to the patient having prostate cancer an ETAR antagonist, an anti-androgen therapy, and castration therapy.

5 Claims, 11 Drawing Sheets

Specification includes a Sequence Listing.

(56) References Cited

OTHER PUBLICATIONS

Boyden LM, Mao J, Belsky J, et al. High bone density due to a mutation in LDL-receptor-related protein 5. *New England Journal of Medicine*. 2002;346(20):1513-1521.
Gong Y, Slee RB, Fukai N, et al. LDL receptor-related protein 5 (LRP5) affects bone accrual and eye development. Cell. 2001;107(4):513-523.
Holmen SL, Giambernardi TA, Zylstra CR, et al. Decreased BMD and Limb Deformities in Mice Carrying Mutations in Both Lrp5 and Lrp6. *Journal of Bone & Mineral Research*. 2004;19(12):2033-2040.
Drake JM, Danke JR, Henry MD. Bone-specific growth inhibition of prostate cancer metastasis by atrasentan. *Cancer Biol Ther*. 2010;9(8):607-614.
Carducci MA, Padley RJ, Breul J, et al. Effect of endothelin—A receptor blockade with atrasentan on tumor progression in men with hormone-refractory prostate cancer: a randomized, phase II, placebo-controlled trial. *Journal of Clinical Oncology*. 2003;21(4):679-689.
Carducci MA, Saad F, Abrahamsson PA, et al. A phase 3 randomized controlled trial of the efficacy and safety of atrasentan in men with metastatic hormone-refractory prostate cancer. *Cancer*. 2007;110(9):1959-1966.
Quinn DI, Tangen CM, Hussain M, et al. Docetaxel and atrasentan versus docetaxel and placebo for men with advanced castration-resistant prostate cancer (SWOG S0421): a randomised phase 3 trial. *Lancet Oncol*. 2013;14(9):893-900.
Lara PN, Jr., Ely B, Quinn DI, et al. Serum biomarkers of bone metabolism in castration-resistant prostate cancer patients with skeletal metastases: results from SWOG 0421. *J Natl Cancer Inst*. 2014;106(4):dju013.
James ND, Caty A, Borre M, et al. Safety and efficacy of the specific endothelin—A receptor antagonist ZD4054 in patients with hormone-resistant prostate cancer and bone metastases who were pain free or mildly symptomatic: a double-blind, placebo-controlled, randomised, phase 2 trial. *Eur Urol*. 2009;55(5):1112-1123.
Nelson JB, Fizazi K, Miller K, et al. Phase 3, randomized, placebo-controlled study of zibotentan (ZD4054) in patients with castration-resistant prostate cancer metastatic to bone. *Cancer*. 2012.
Clines GA, Mohammad KS, Grunda JM, et al. Regulation of postnatal trabecular bone formation by the osteoblast endothelin A receptor. *Journal of Bone and Mineral Research*. 2011;26(10):2523-2536.
Klein H, Bressel M, Kastendieck H, Voigt KD. Androgens, adrenal androgen precursors, and their metabolism in untreated primary tumors and lymph node metastases of human prostatic cancer. *Am J Clin Oncol*. 1988;11 Suppl 2:S30-36.
Dillard PR, Lin MF, Khan SA. Androgen-independent prostate cancer cells acquire the complete steroidogenic potential of synthesizing testosterone from cholesterol. *Mol Cell Endocrinol*. 2008;295(1-2):115-120.
Stuchbery R, McCoy PJ, Hovens CM, Corcoran NM. Androgen synthesis in prostate cancer: do all roads lead to Rome? *Nat Rev Urol*. 2017;14(1):49-58.
Van Weerden WM, Bierings HG, van Steenbrugge GJ, de Jong FH, Schroder FH. Adrenal glands of mouse and rat do not synthesize androgens. *Life Sci*. 1992;50(12):857-861.
Sedelaar JPM, Dalrymple SS, Isaacs JT. Of mice and men-warning: Intact versus castrated adult male mice as xenograft hosts are equivalent to hypogonadal versus abiraterone treated aging human males, respectively. *The Prostate*. 2013;73:1316-1325.
Zhau HE, Li CL, Chung LW. Establishment of human prostate carcinoma skeletal metastasis models. *Cancer*. 2000;88(12 Suppl):2995-3001.
Xu J, Wang R, Xie ZH, et al. Prostate cancer metastasis: role of the host microenvironment in promoting epithelial to mesenchymal transition and increased bone and adrenal gland metastasis. *Prostate*. 2006;66(15):1664-1673.
Guise TA, Yin JJ, Taylor SD, et al. Evidence for a causal role of parathyroid hormone-related protein in the pathogenesis of human breast cancer-mediated osteolysis. *Journal of Clinical Investigation*. 1996;98(7):1544-1549.
Morris CD, Rose A, Curwen J, Hughes AM, Wilson DJ, Webb DJ. Specific inhibition of the endothelin A receptor with ZD4054: clinical and pre-clinical evidence. *Br J Cancer*. 2005;92(12):2148-2152.
Rosano L, Di Castro V, Spinella F, Nicotra MR, Natali PG, Bagnato A. ZD4054, a specific antagonist of the endothelin A receptor, inhibits tumor growth and enhances paclitaxel activity in human ovarian carcinoma in vitro and in vivo. *Mol Cancer Ther*. 2007;6(7):2003-2011.
Growcott JW. Preclinical anticancer activity of the specific endothelin A receptor antagonist ZD4054. *Anticancer Drugs*. 2009;20(2):83-88.
Haque SU, Dashwood MR, Heetun M, et al. Efficacy of the specific endothelin a receptor antagonist zibotentan (ZD4054) in colorectal cancer: a preclinical study. *Mol Cancer Ther*. 2013;12(8):1556-1567.
Dai J, Hensel J, Wang N, Kruithof-de Julio M, Shiozawa Y. Mouse models for studying prostate cancer bone metastasis. *Bonekey Rep*. 2016;5:777.
Grunda JM, Wang D, Clines GA. Development and characterization of murine models of medulloblastoma extraneural growth in bone. *Clin Exp Metastasis*. 2013;30(6):769-779.
Hewitson TD, Zhao C, Wigg B, et al. Relaxin and castration in male mice protect from, but testosterone exacerbates, age-related cardiac and renal fibrosis, whereas estrogens are an independent determinant of organ size. *Endocrinology*. 2012;153(1):188-199.
Zhang X, Thatcher S, Wu C, Daugherty A, Cassis LA. Castration of male mice prevents the progression of established angiotensin II-induced abdominal aortic aneurysms. *J Vasc Surg*. 2015;61(3):767-776.
Esvelt MA, Freeman ZT, Pearson AT, et al. The Endothelin—A Receptor Antagonist Zibotentan Induces Damage to the Nasal Olfactory Epithelium Possibly Mediated in Part through Type 2 Innate Lymphoid Cells. *Toxicol Pathol*. 2018:192623318816295.
Yang F, Li X, Sharma M, et al. Linking beta-catenin to androgen-signaling pathway. *J Biol Chem*. 2002;277(13):11336-11344.
Singh R, Bhasin S, Braga M, et al. Regulation of myogenic differentiation by androgens: cross talk between androgen receptor/beta-catenin and follistatin/transforming growth factor-beta signaling pathways. *Endocrinology*. 2009;150(3):1259-1268.
Liu XH, Kirschenbaum A, Yao S, Liu G, Aaronson SA, Levine AC. Androgen-induced Wnt signaling in preosteoblasts promotes the growth of MDA-PCa-2b human prostate cancer cells. *Cancer Res*. 2007;67(12):5747-5753.
Wei A, Gu Z, Li J, et al. Clinical Adverse Effects of Endothelin Receptor Antagonists: Insights From the Meta-Analysis of 4894 Patients From 24 Randomized Double-Blind Placebo-Controlled Clinical Trials. *J Am Heart Assoc*. 2016;5(11).
Rosol TJ, Tannehill-Gregg SH, LeRoy BE, Mandl S, Contag CH. Animal models of bone metastasis. *Cancer*. 2003;97(3 Suppl):748-757.
Gelman IH. How the TRAMP Model Revolutionized the Study of Prostate Cancer Progression. *Cancer Res*. 2016;76(21):6137-6139.
Simmons JK, Hildreth BE, 3rd, Supsavhad W, et al. Animal Models of Bone Metastasis. *Vet Pathol*. 2015;52(5):827-841.
Xiang L, Gilkes DM. The Contribution of the Immune System in Bone Metastasis Pathogenesis. *Int J Mol Sci*. 2019;20(4).
Smith MR, Lee WC, Brandman J, Wang Q, Botteman M, Pashos CL. Gonadotropin-releasing hormone agonists and fracture risk: a claims-based cohort study of men with nonmetastatic prostate cancer. *Journal of Clinical Oncology*. 2005;23(31):7897-7903.
U.S. Appl. No. 62/855,105, filed May 31, 2019, Gregory Clines (U.S. Government as Represented by the Department of Veterans Affairs).

* cited by examiner

| Group comparisons | | | p value |
|---|---|---|---|
| Zibo+Castr | vs. | Zibo+Sham | **<0.001** |
| Zibo+Castr | vs. | Veh+Castr | **<0.001** |
| Zibo+Castr | vs. | Veh+Sham | **<0.001** |
| Zibo+Sham | vs. | Veh+Castr | **<0.001** |
| Zibo+Sham | vs. | Veh+Sham | 0.187 |
| Veh+Castr | vs. | Veh+Sham | **<0.001** |

| Group comparisons | | | p value |
|---|---|---|---|
| Zibo+Castr | vs. | Zibo+Sham | **0.0045** |
| Zibo+Castr | vs. | Veh+Castr | **0.0050** |
| Zibo+Castr | vs. | Veh+Sham | 0.340 |
| Zibo+Sham | vs. | Veh+Castr | 0.329 |
| Zibo+Sham | vs. | Veh+Sham | **0.0171** |
| Veh+Castr | vs. | Veh+Sham | 0.160 |

A

| Group comparisons | | | p value |
|---|---|---|---|
| Zibo+Castr | vs. | Zibo+Sham | **0.0149** |
| Zibo+Castr | vs. | Veh+Castr | 0.0848 |
| Zibo+Castr | vs. | Veh+Sham | 0.119 |
| Zibo+Sham | vs. | Veh+Castr | 0.322 |
| Zibo+Sham | vs. | Veh+Sham | 0.745 |
| Veh+Castr | vs. | Veh+Sham | 0.764 |

B

| Group comparisons | | | p value |
|---|---|---|---|
| Zibo+Castr | vs. | Zibo+Sham | **0.0250** |
| Zibo+Castr | vs. | Veh+Castr | 0.293 |
| Zibo+Castr | vs. | Veh+Sham | 0.869 |
| Zibo+Sham | vs. | Veh+Castr | 0.215 |
| Zibo+Sham | vs. | Veh+Sham | 0.179 |
| Veh+Castr | vs. | Veh+Sham | 0.641 |

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 1

ccggagagga gacttcacag                                                   20


<210> SEQ ID NO 2
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 2

ggaaattggg gtaggaagga                                                   20


<210> SEQ ID NO 3
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 3

cagggtgcgg agaaggttca aggg                                              24


<210> SEQ ID NO 4
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 4

cttagaggac acgttgtgag caat                                              24
```

COMPOSITIONS AND METHODS COMPRISING ENDOTHELIN A RECEPTOR ANTAGONISTS AND ANDROGEN THERAPIES

CROSS-REFERENCE TO RELATED APPLICATIONS

This is a U.S. National Phase Application of International Application No. PCT/US2020/035042, filed May 29, 2020, which claims the benefit of U.S. Provisional Patent Application No. 62/855,105, filed on May 31, 2019, each of which are incorporated by reference herein in their entireties.

STATEMENT REGARDING FEDERALLY SPONSORED RESEARCH

This invention was made with government support under I01BX001370 awarded by the U.S. Department of Veterans Affairs. The government has certain rights in the invention.

REFERENCE TO SEQUENCE LISTING

The Sequence Listing submitted Apr. 25, 2025 as a text file named "37759.0238U2 Sequence Listing.tx," created on Apr. 24, 2025, and having a size of 1,245 bytes is hereby incorporated by reference pursuant to 37 C.F.R. § 1.52(e) (5).

BACKGROUND

Prostate cancer is the most common deadly cancer of men and is unique in its affinity to bone. Bone metastasis is painful and associated with significant morbidity. Bone metastasis occurs in up to 90% of men with advanced prostate cancer compared to significantly lower rates of skeletal metastasis with other common cancers such as lung and colon. Bone provides prostate cancer cells with a conducive environment for growth. Prostate cancer cells in turn alter the bone microenvironment resulting in primarily osteosclerotic lesions.

Men with advanced prostate cancer and bone metastases have higher circulating endothelin-1 (ET-1) compared to men with early stage disease. ET-1 is a 21 amino acid secreted protein well known as a potent vasoconstrictor. ET-1 is one factor involved in the osteosclerotic skeletal response to invading prostate cancer cells. ET-1 promotes pathologic osteoblast proliferation and new bone formation through activation of the osteoblast endothelin A receptor ($ET_AR$) and subsequent reduction in secreted dickkopf homolog 1 (DKK1), a Wnt signaling inhibitor. The result is an increase in Wnt signaling, a critical signaling pathway that directs the commitment and differentiation of mesenchymal cells to osteoblasts.

Drake, et al reported the importance of ET-1 in an animal model of prostate cancer bone metastasis. The $ET_AR$-selective antagonist, atrasentan, significantly reduced bone lesions but not lesions outside of the skeleton such as adrenal gland and liver. Similar results were reported in a mouse model of breast cancer osteosclerotic bone metastasis. Atrasentan blocked the formation of osteoblastic lesions, but not tumor progression outside of bone. These data indicate that ET-1/$ET_AR$ signaling is critical for bone metastasis but not for metastasis outside the skeleton.

The results of the above animal studies prompted human clinical trials examining endothelin-selective antagonists in prostate cancer. In a phase 2 trial of 288 men with castrate-resistant prostate cancer (CRPC), atrasentan increased the time to progression from 129 to 196 days and delayed prostate-specific antigen (PSA) progression. This was followed by a phase 3 trial of 809 men with metastatic disease, most of whom had bone metastasis. Atrasentan did not reduce the primary endpoint of time to progression, but secondary analyses supported that atrasentan did reduce bone alkaline phosphatase progression. In a separate trial of men with metastatic CRPC treated with docetaxel, atrasentan did not improve overall or progression-free survival compared to placebo. However, a survival benefit of atrasentan in patients with the highest circulating levels of bone turnover markers was reported.

Similar studies were conducted with the $ET_AR$-specific antagonist zibotentan in men with prostate cancer. Zibotentan increased overall survival from 17.3 to 24.5 months in 312 men with metastatic CRPC in a phase 2 trial. But, a phase 3 trial studying zibotentan as a monotherapy in men with non-metastatic disease was stopped early due to lack of effect in the primary outcome of overall survival. One reason for the failure of the phase 3 trials is that the ET-1 axis is critical for bone metastasis but not for tumor growth outside of bone, and is consistent with the reported pre-clinical data.

Another possible reason for the failure of these trials is due to a complex interaction between endothelin and androgen signaling. Sexual dimorphism regarding the effects of targeted-inactivation of osteoblast $ET_AR$—increased bone acquisition in gonadal intact male mice, but reduced bone acquisition in castrated male mice. This effect was not observed with castration in females. An interpretation of this data is that while both ET-1/$ET_AR$ and androgen signaling each contribute to bone formation, an interaction exists whereby endothelin signaling may limit the anabolic effects of androgen on bone.

Based on this model, a potential limitation of the $ET_AR$ antagonist clinical trials was inadequate androgen withdrawal. Androgen deprivation therapy (ADT) is standard treatment in men with advanced prostate cancer. In the U.S. and Europe, gonadotropin-releasing hormone (GnRH) agonists are the most common method of androgen deprivation. However, GnRH agonists do not result in complete androgen deprivation. Adrenal androgens and even prostate cancer production of androgens from adrenal androgen precursors also remain constant sources of prostate cancer stimulation. If the proposed model of ET-1/$ET_AR$ and androgen signaling interaction is correct, $ET_AR$ blockade would amplify the effects of existing androgen—even limited amounts—to promote prostate cancer growth in bone and negate the effects of ADT. An advantage of the mouse is that castration of male mice results in complete androgen deprivation. Unlike humans, mice do not synthesize adrenal androgens.

Compositions comprising and the methods of using an $ET_AR$ antagonist, in combination with a complete androgen deprivation therapy, are disclosed herein.

BRIEF SUMMARY

Disclosed are compositions comprising an endothelin A receptor ($ET_AR$) antagonist, an anti-androgen therapy, and chemical castration therapy.

Also disclosed are compositions comprising an $ET_AR$ antagonist, copackaged or coformulated with an anti-androgen therapy.

Disclosed are methods of preventing prostate cancer metastasis comprising administering to a subject having prostate cancer an $ET_AR$ antagonist, an anti-androgen therapy, and castration therapy.

Also disclosed are methods of increasing survival in a prostate cancer patient, comprising administering to the patient having prostate cancer an $ET_AR$ antagonist, an anti-androgen therapy, and castration therapy.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
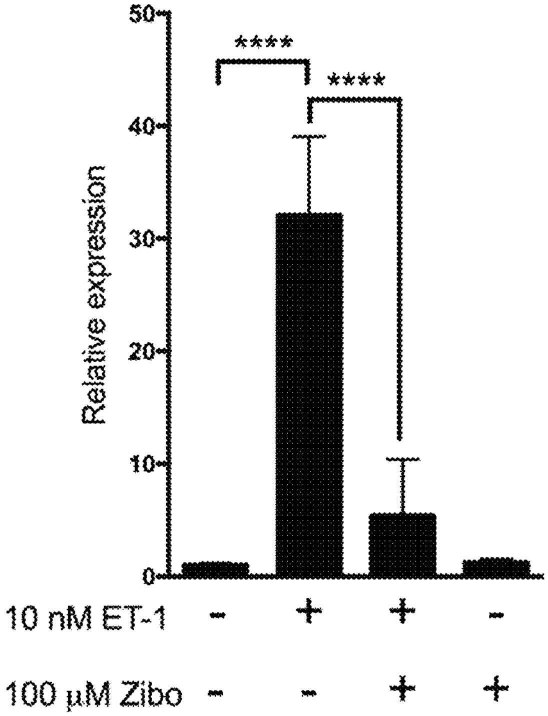
FIG. 1 shows that zibotentan blocks $ET_AR$ signaling in mouse osteoblasts. Calvarial osteoblasts were cultured and pre-treated with or without 100 μM zibotentan for six hours followed by treatment with or without 10 nM ET-1 for four hours. RNA has then harvested and analyzed for the expression of Il-6, a marker of ET-1 action in osteoblasts. Il-6 expression was normalized to the housekeeping gene Rpl32. Data was analyzed using one-way ANOVA followed by Tukey's multiple comparison test.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a nucleic acid" includes a plurality of such nucleic acids, reference to "the nucleic acid" is a reference to one or more nucleic acids and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

The term "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient."

"Peptide" as used herein refers to any polypeptide, oligopeptide, gene product, expression product, or protein. A peptide is comprised of consecutive amino acids. The term "peptide" encompasses recombinant, naturally occurring and synthetic molecules.

In addition, as used herein, the term "peptide" refers to amino acids joined to each other by peptide bonds or modified peptide bonds, e.g., peptide isosteres, etc. and may contain modified amino acids other than the 20 gene-encoded amino acids. The peptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given peptide. Also, a given peptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins-Structure and Molecular Properties 2nd Ed., T. E. Creighton, W. H. Freeman and Company, New York (1993); Posttranslational Covalent Modification of Proteins, B. C. Johnson, Ed., Academic Press, New York, pp. 1-12 (1983)).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof By an "effective amount" of a composition as provided herein is meant a sufficient amount of the composition to provide the desired effect. The exact amount required will vary from subject to subject, depending on the species, age, and general condition of the subject, the severity of disease (or underlying genetic defect) that is being treated, the particular composition used, its mode of administration, and the like. Thus, it is not possible to specify an exact "effective amount." However, an appropriate "effective amount" may be determined by one of ordinary skill in the art using only routine experimentation.

By "treat" is meant to administer a peptide, nucleic acid, compound, or composition of the invention to a subject, such as a human or other mammal (for example, an animal model), that has an increased susceptibility for developing a disease or disorder, or that has a disease or disorder, in order to prevent or delay a worsening of the effects of the disease or condition, or to partially or fully reverse the effects of the disease. For example, the disease or disorder can be a hormone-related disease or disorder. In some aspects, a hormone-related disease or disorder can be cancer.

By "prevent" is meant to minimize the chance that a subject who has an increased susceptibility for developing a disease or disorder will develop the disease or disorder.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In some aspects, a preparation can be administered in an effective amount.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Compositions

Disclosed are compositions comprising an endothelin A receptor ($ET_AR$) antagonist, an anti-androgen therapy, and chemical castration therapy. The combination of anti-androgen therapy and chemical castration therapy results in a complete androgen deprivation therapy. A complete androgen deprivation therapy results in an inactivation, inhibition, depletion, or blocking of total androgen in a subject.

Also disclosed are compositions comprising an $ET_AR$ antagonist, copackaged or coformulated with an anti-androgen therapy.

The disclosed compositions can have any of the $ET_AR$ antagonists, anti-androgen therapy, and/or chemical castration therapies described herein.

In some aspects, the $ET_AR$ antagonist can be an endothelin-1 (ET-1) antagonist. In some aspects, the $ET_AR$ antagonist blocks ET-1 from binding to $ET_AR$. In some aspects, the ET-1 antagonist blocks ET-1 synthesis or secretion. In some aspects, the $ET_AR$ antagonist can be, but is not limited to, zibotentan, atrasentan, or derivatives thereof. In some aspects, the $ET_AR$ antagonist can be $ET_AR$ antagonists that also block the ETBR. For example, $ET_AR$ antagonists that block the ETBR can be, but are not limited to, bosentan, ambrisentan, macitentan, or derivatives thereof.

In some aspects, the $ET_AR$ antagonist can be a nucleic acid, peptide, or compound.

In some aspects, the anti-androgen therapy can be a nucleic acid, peptide, or compound that inhibits, inactivates, depletes, or blocks the effects of androgens (e.g. adrenal androgens or testicular androgens). In some aspects, the anti-androgen therapy can be a nucleic acid, peptide, or compound that inhibits, inactivates, depletes, or blocks androgen produced by the adrenal gland (i.e. adrenal androgen). In some aspects, the anti-androgen therapy can be a nucleic acid, peptide, or compound that inhibits, inactivates, depletes, or blocks androgen produced by the testes gland (i.e. testicular androgen). In some aspects, the anti-androgen therapy can be a nucleic acid, peptide, or compound that inhibits, inactivates, depletes, or blocks androgen produced by the adrenal gland (i.e. adrenal androgen) and do not inhibits, inactivates, depletes, or blocks or only partially block androgen produced by the testes gland (i.e. testicular androgen). For example, the anti-androgen therapy can be, but is not limited to, abiraterone acetate, enzalutamide, apalutamide, darolutamide, or derivatives thereof. In some aspects, the anti-androgen therapy blocks androgen synthesis. For example, an anti-androgen therapy that blocks androgen synthesis can be abiraterone acetate. In some aspects, the anti-androgen therapy blocks androgen action at the receptor level. For example, an anti-androgen therapy that blocks androgen action at the receptor level can be enzalutamide or a derivative thereof.

In some aspects, the chemical castration therapy can be luteinizing hormone-releasing hormone (LHRH) agonists or antagonists. LHRH activates the synthesis of luteinizing hormone (LH) which induces the formation of testosterone, an androgen. LHRH agonists can produce a sudden increase on levels of testosterone (i.e. an androgen) followed by a huge falling, process called flare, whereas LHRH antagonists can decrease directly the amount of testosterone. An example of a LHRH can be a gonadotropin releasing hormone (GnRH). Thus, in some aspects, the chemical castration therapy can be GnRH agonists or antagonists. In some aspects, the chemical castration therapy is leuprorelin, goserelin, triptorelin, histrelin, buserelin, degarelix, or derivatives thereof.

C. Methods

Disclosed are methods of preventing prostate cancer metastasis comprising administering to a subject having prostate cancer an $ET_AR$ antagonist, an anti-androgen therapy, and castration therapy. In some aspects, the prostate cancer metastasis is bone metastasis.

Also disclosed are methods of increasing survival in a prostate cancer patient, comprising administering to the patient having prostate cancer an ETAR antagonist, an anti-androgen therapy, and castration therapy. In some aspects, increasing survival in a prostate cancer patient can include extending the patients lifespan in view of the severity of their disease. Thus, in some aspects, increasing survival can include extending a patient's life by 1, 2, 3, 4, 5, 6, 7, 8, 9, 10, 11, or 12 months. In some aspects, increasing survival can include extending a patient's life by 1, 2, 3, 4, 5, 6, 7, 8, 9, 10, 11, 12, 13, 14, 15, 16, 17, 18, 19, 20, 21, 22, 23, 24, 25 years.

In some aspects, the subject has prostate cancer. In some aspects, the subject can have advanced prostate cancer. In some aspects, the subject can have castrate-resistant prostate cancer (CRPC).

In some aspects, the $ET_AR$ antagonist and the anti-androgen therapy can be administered simultaneously. In some aspects, the $ET_AR$ antagonist and the anti-androgen therapy can be co-administered in a single formulation. In some aspects, the $ET_AR$ antagonist and the anti-androgen therapy can be administered in separate formulations. Thus, regardless of whether the $ET_AR$ antagonist and the anti-androgen therapy are formulated together in a single formulation or in separate formulations, they can still be administered simultaneously. Simultaneous administration can include administering the the $ET_AR$ antagonist and the anti-androgen therapy at the exact same time, within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes of each other.

In some aspects, the $ET_AR$ antagonist and the anti-androgen therapy administered at different times. Administering the $ET_AR$ antagonist and the anti-androgen therapy at different times can include administering them at least 30 minutes, 1, 2, 3, 4, 5, 6, 7, 8, 9, 10, 11, 12, 13, 14, 15, 16, 17, 18, 19, 20, 21, 22, 23, or 24 hours apart. In some aspects, the $ET_AR$ antagonist and the anti-androgen therapy can be administered 1, 2, 3, 4, 5, 6, or 7 days apart. In some aspects, the $ET_AR$ antagonist and the anti-androgen therapy can be administered 1, 2, 3, or 4 weeks apart. In some aspects, the $ET_AR$ antagonist and the anti-androgen therapy can be administered 1, 2, 3, 4, 5, 6, 7, 8, 9, 10, 11, or 12 months apart.

In some aspects, any of the $ET_AR$ antagonists described herein can be used in the disclosed methods. For example, the $ET_AR$ antagonist can be an ET-1 antagonist. In some aspects, the $ET_AR$ antagonist blocks ET-1 from binding to $ET_AR$. In some aspects, the ET-1 antagonist blocks ET-1 synthesis or secretion. In some aspects, the $ET_AR$ antagonist can be, but is not limited to, zibotentan or atrasentan. In some aspects, the $ET_AR$ antagonist can be $ET_AR$ antagonists that also block the $ET_BR$. For example, $ET_AR$ antagonists that block the $ET_BR$ can be, but are not limited to, bosentan, ambrisentan, and macitentan.

In some aspects, the atrasetan can be administered in a dose of 10 mg PO daily. In some aspects, the zibotentan can be administered in a dose of 10 mg PO daily.

In some aspects, any of the anti-androgen therapy described herein can be used in the disclosed methods. In some aspects, the anti-androgen therapy can be a nucleic acid, peptide, or compound that inhibits, inactivates, depletes, or blocks androgen produced by the adrenal gland (i.e. adrenal androgen). For example, the anti-androgen therapy can be, but is not limited to, abiraterone acetate, enzalutamide, apalutamide, or darolutamide. In some aspects, the anti-androgen therapy blocks androgen synthesis. For example, an anti-androgen therapy that blocks androgen synthesis can be abiraterone acetate. In some aspects, the anti-androgen therapy blocks androgen action at the receptor level. For example, an anti-androgen therapy that blocks androgen action at the receptor level can be enzalutamide.

In some aspects, the abiraterone acetate can be administered in a dose of 500-1000 mg PO daily. In some aspects, the enzalutamide can be administered in a dose of 160 mg PO daily. In some aspects, the apalutamide can be administered in a dose of 240 mg PO daily. In some aspects, the darolutamide can be administered in a dose of 600 mg PO twice daily.

In some aspects, the castration therapy can be chemical castration, physical castration, or a combination thereof. In some aspects, the castration therapy can be chemical castration therapy. For example, the chemical castration therapy can be GnRH agonists or antagonists. In some aspects, the chemical castration therapy can be leuprorelin, goserelin, triptorelin, histrelin, buserelin, or degarelix.

D. Delivery of Compositions

In the methods described herein, delivery (or administration) of the compositions to cells can be via a variety of mechanisms. As defined above, disclosed herein are compositions comprising any one or more of the peptides, nucleic acids, and/or vectors described herein can be used to produce a composition which can also include a carrier such as a pharmaceutically acceptable carrier. For example, disclosed are pharmaceutical compositions, comprising the peptides disclosed herein, and a pharmaceutically acceptable carrier.

For example, the compositions described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG: PC: Cholesterol: peptide or PC: peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

E. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing any of the disclosed compositions. The kits can contain an ETAR antagonist and/or an anti-androgen therapy.

Examples

F. Materials and Methods

1. RT-PCR Analysis

Murine calvarial osteoblasts were collected and cultured as previously described 7. Two days post-confluence, osteoblasts were treated in triplicate with or without 100 μM zibotentan for six hours. This was followed by treatment with or without 10 nM ET-1 for four hours. RNA was collected using Direct-zol™ RNA MiniPrep Plus kit (Zymo, Irvine, CA) according to the manufacturer's directions. RNA was then analyzed by RT-PCR using the iTaq Universal SYBR Green One-Step Kit and a C1000 Thermal Cycler with a CFX96 fluorescent real-time attachment (Bio-Rad, Hercules, CA) using the following primers: Il-6: F, ccg gag agg aga ctt cac ag (SEQ ID NO:1); R, gga aat tgg ggt agg aag ga (SEQ ID NO: 2); and Rpl32: F, cag ggt gcg gag aag gtt caa ggg (SEQ ID NO:3); R, ctt aga gga cac gtt gtg agc aat (SEQ ID NO:4). Rpl32 was utilized as the normalization gene that has unvaried expression. Changes in mRNA concentration were determined by subtracting the Ct (threshold cycle) of Il-6 from the Ct of Rpl32 ($\Delta$=$Ct_{Il-6}$-$Ct_{Rp132}$). The mean of $\Delta_{control}$ Was subtracted from each of the $\Delta_{experimental}$ reactions (mean $\Delta_{control}$−$\Delta_{experimental}$=ε). The fold difference was calculated as 28.

2. Cell Culture

The $ARCaP_M$ cell line (Novicure Biotechnology, Birmingham, AL) was maintained in MCaP growth medium (Novicure Biotechnology) supplemented with 5% fetal bovine serum (FBS). The $ARCaP_M$ prostate cancer cell line, when inoculated into nude mice, produces mixed osteosclerotic/osteolytic skeletal lesions[25,26].

3. Animals

All animal experiments were performed in accordance with established protocols approved by the Institutional Animal Care and Use Committee at the Ann Arbor Veterans Affairs Medical Center. Mice were housed four per cage in an AAALAC accredited animal facility in temperature- and humidity-controlled rooms maintained on a 12:12-hour light:dark cycle. Animals were housed in static microisolator cages and had continuous free access to water and food (Forumulab Diet 5008, Purina LabDiet®, St.Louis, MO). Environmental enrichment included BioServ® plastic shelters of various sizes and configurations, and autoclaved empty paper tubes.

Previous data indicate that n=10 mice yields statistical significance with respect to bone histomorphometric endpoints. An additional two mice were added to each experimental group to account for expected losses with intracardiac inoculation (12 mice/group; 48 mice total).

Forty-eight HSD athymic nude male mice were obtained from Harlan Sprague Dawley (Envigo, Indianapolis, IN) after undergoing castration or sham surgery. At five weeks of age, mice were anesthetized using isoflurane vaporizer anesthesia. $ARCaP_M$ prostate cancer cells were washed, resuspended in PBS, and inoculated into the left cardiac ventricle at a volume of 100 μl containing $1\times10^5$ cells, as previously described. Starting at seven days post-inoculation, mice were weighed every 2-3 days.

4. Zibotentan and Vehicle Control Treatments

Zibotentan is an $ET_AR$-specific antagonist and was obtained from AstraZeneca (Cambridge, England). Zibotentan was dissolved in 1% polysorbate 80 at a concentration of 5 mg/ml. Mice in the treatment group received zibotentan 25 mg/kg/day. Mice in the vehicle control group received an equivalent volume of 1% polysorbate 80 via gavage. Gavage treatments were started two days after the intracardiac inoculations (5 weeks+2 days of age) seven days/week. The dosing scheduled was changed to five days/week at 59 days post-inoculation.

5. Radiographic Imaging

Mice were anesthetized using an isoflurane vaporizer anesthetic unit and underwent radiographic imaging using a Faxitron UltraFocus 60 Digital Radiographic Unit (Faxitron, Tucson, AZ) every 2-4 weeks with attention paid to the appearance of sclerotic or lytic skeletal lesions.

6. Euthanasia Criteria

The mice were euthanized according to the following criteria: development of significant skeletal lesions that resulted in either fracture or paraplegia, loss of more than 15% of baseline weight, lethargy, hunched posture, dehydration, or if a tumor interfered with the ability to acquire food or water.

7. Bone Histology and Histomorphometry

Following euthanasia, mouse femora, tibiae, humeri, spines and other bones were harvested and fixed in 10% buffered formalin for 48 hours and decalcified in Immunocal (Decal Chemical Corp, Suffern, NY) for an additional 48 hours. Bones were rinsed, processed and paraffin embedded. Blocks were cut into 5 μm sections, mounted onto charged glass slides, and air-dried overnight.

Static histomorphometric analysis was performed on embedded samples stained with hematoxylin, eosin, and orange G, a bone matrix stain. Images of the samples were taken at 4X with Nikon Eclipse 90i upright microscope and Nikon HD Cooled Color Digital Camera DXM1200C paired with Nikon ACT-1C software. Each sample produced 10 to 30 tiled scans of the whole specimen and were stitched using Adobe Photoshop CC. Tumor area was traced and measured on Adobe Photoshop CC with Cintiq 22HD touch (Wacom) tablet PC and stylus. Then, measured tumor area was divided by each subject's age in days for further statistical analysis.

8. Serum ET-1 ELISA Measurements

Blood was collected at euthanasia. Sera was collected using serum-separator centrifuge tubes (BD Microtainer®, SST, Becton Dickinson, Franklin Lakes, NJ), and frozen at −80° C. for later analyses. ET-1 concentration was measured in thawed sera using an ET-1 colorimetric ELISA kit (R&D Systems, Minneapolis, MN) and a BioTek Synergy HTX plate reader (Winooski, VT).

9. Statistical Analyses

Data sets were analyzed for normality using the D'Agostino-Pearson method. Data sets were analyzed by one-way ANOVA followed by the Tukey's multiple comparison when data sets followed normal distribution. Data sets containing two independent variables were analyzed by two-way ANOVA using Sidak multiple comparison testing. Data sets with categorical outcomes were analyzed by the Fisher's exact test. Survival and event analyses were performed using the Kaplan-Meier method with the Mantel-Cox test. A p value≤0.05 was considered significant. Data was analyzed using SAS Software (SAS Institute, Cary, NC) or GraphPad Prism Software (GraphPad Software, Inc., La Jolla, CA). An a cutoff value of 0.05 was used for all analyses and reported p values were applied to two-tailed analyses.

G. Results

1. Zibotentan Blocks Osteoblast $ET_AR$ Signaling

Zibotentan is an $ET_AR$-specific small molecule inhibitor that has no affinity for the endothelin B receptor ($ET_BR$), the other receptor for endothelin ligands, and has been extensively tested in other animal models to block $ET_AR$ signaling. Atrasentan, another $ET_AR$-specific antagonist, was reported to block the anabolic effects of ET-1 on the osteoblast. We confirmed the actions of zibotentan on osteoblasts by measuring the expression of interleukin-6 (Il-6), a marker of ET-1 action on the osteoblast. Pre-treatment of zibotentan prevented the increase in Il-6 expression with ET-1 (FIG. 1).

2. Zibotentan and Castration in a Prostate Cancer Bone Metastasis Model

Animal models that closely mimic human prostate cancer bone metastasis have been valuable in the mechanistic discovery of critical factors that drive metastatic growth. One such model utilizes the $ARCaP_M$ prostate cancer cell line, an castrate-resistant prostate cancer cell line that forms mixed osteosclerotic/osteolytic skeletal lesions after inoculation into the left cardiac ventricle. $ARCaP_M$ cells also secrete a significant amount of ET-1 (176±20 pg/1×$10^6$ cells/48 hours) making this particular cell line useful for studying the effects of endothelin blockade on the development of skeletal lesions.

Figure 2:
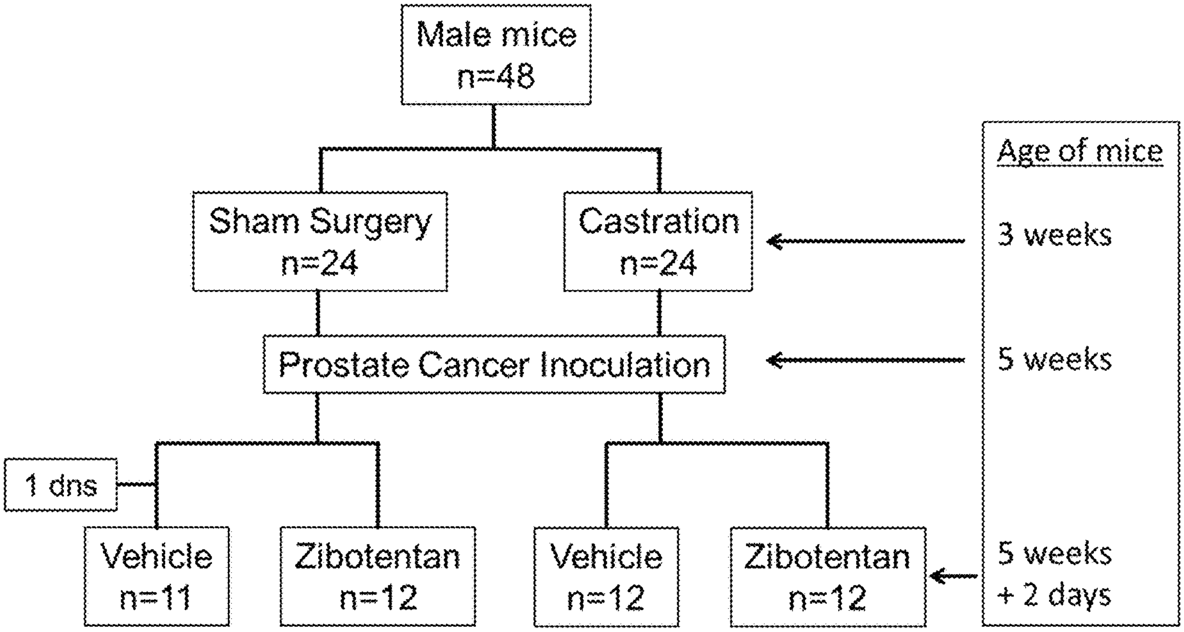
FIG. 2 shows a treatment strategy. Forty-eight male athymic nude mice either underwent castration or sham surgery at four weeks of age. At 5 weeks of age, mice were inoculated with $ARCaP_M$ prostate cancer cell line into the left cardiac ventricle. One mouse in the Vehicle+Sham surgery group did not survive (dns) the inoculation. Two days later, mice began zibotentan 25 mg/kg/day or vehicle control by gavage.

Forty-eight male athymic nude mice underwent castration (24 mice) or sham surgery (24 mice) at three weeks of age. At five weeks of age, $ARCaP_M$ prostate cancer cells (1×$10^5$ cells in 100 μl) were inoculated into the left cardiac ventricle. A single mouse did not survive the inoculation. Two days later, zibotentan 25 mg/kg/day or vehicle control treatments by gavage were started. This strategy produced four experimental groups: vehicle+sham (Veh+Sham), vehicle+castrate (Veh+Castr), zibotentan+sham (Zibo+Sham), and zibotentan+castrate (Zibo+Castr) (FIG. 2).

Figure 3:
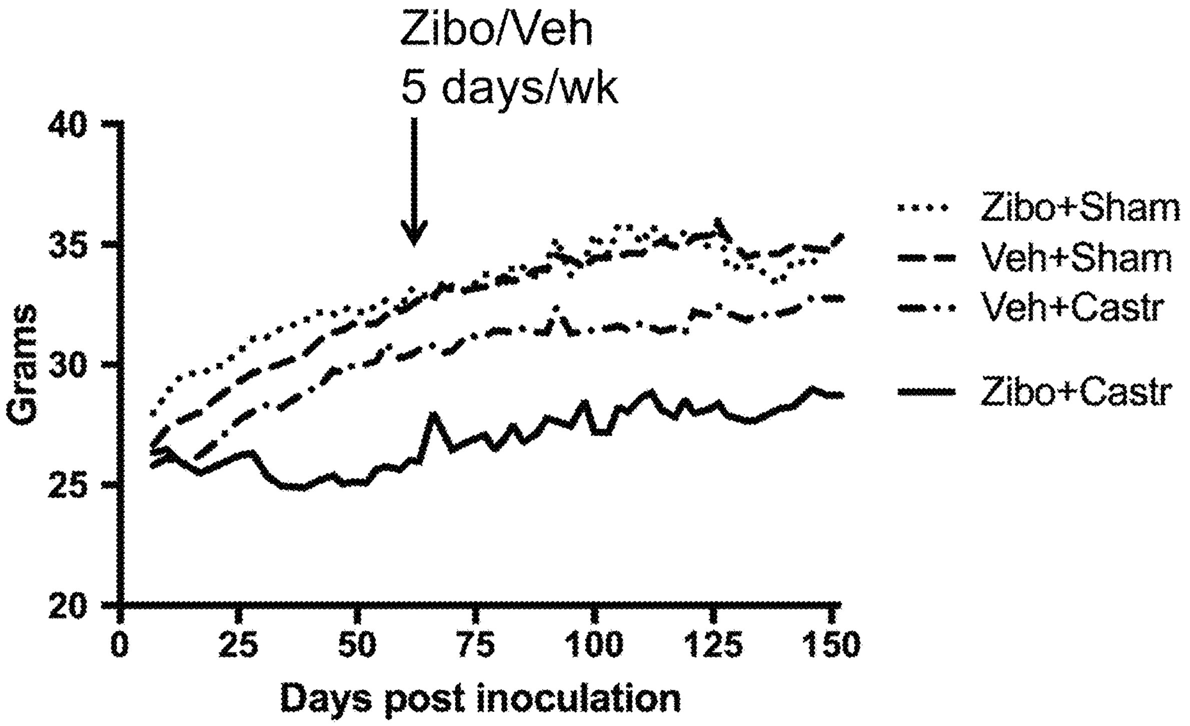
FIG. 3 shows changes in body weight. Mice body weights were measured starting at 7 days post-inoculation and continued every 2-3 days until the completion of the experiment at 152 days. Two days after inoculation, mice began to receive zibotentan or vehicle control. Due to potential adverse effects in the Zibo+Castr group, the dosing was reduced to 5 days/week starting at day 59 post inoculation. Veh=vehicle control; Zibo=zibotentan; Sham=sham surgery; Castr=castration

3. Effects of Zibotentan and Castration on the Development of Bone Lesions and Survival The mice underwent radiographic imaging every 2-4 weeks to monitor for the development of bone lesions. Mice were also monitored frequently for abnormal behavior indicating the presence of a large tumor burden. Euthanasia was performed according to pre-determined humane endpoints—15% weight loss, paralysis, skeletal fractures, or any other signs of distress. Mice were weighed every 2-3 days (FIG. 3). As expected, mice in the castration groups had less weight gain compared to the sham groups, as has been reported elsewhere.

Figure 4:
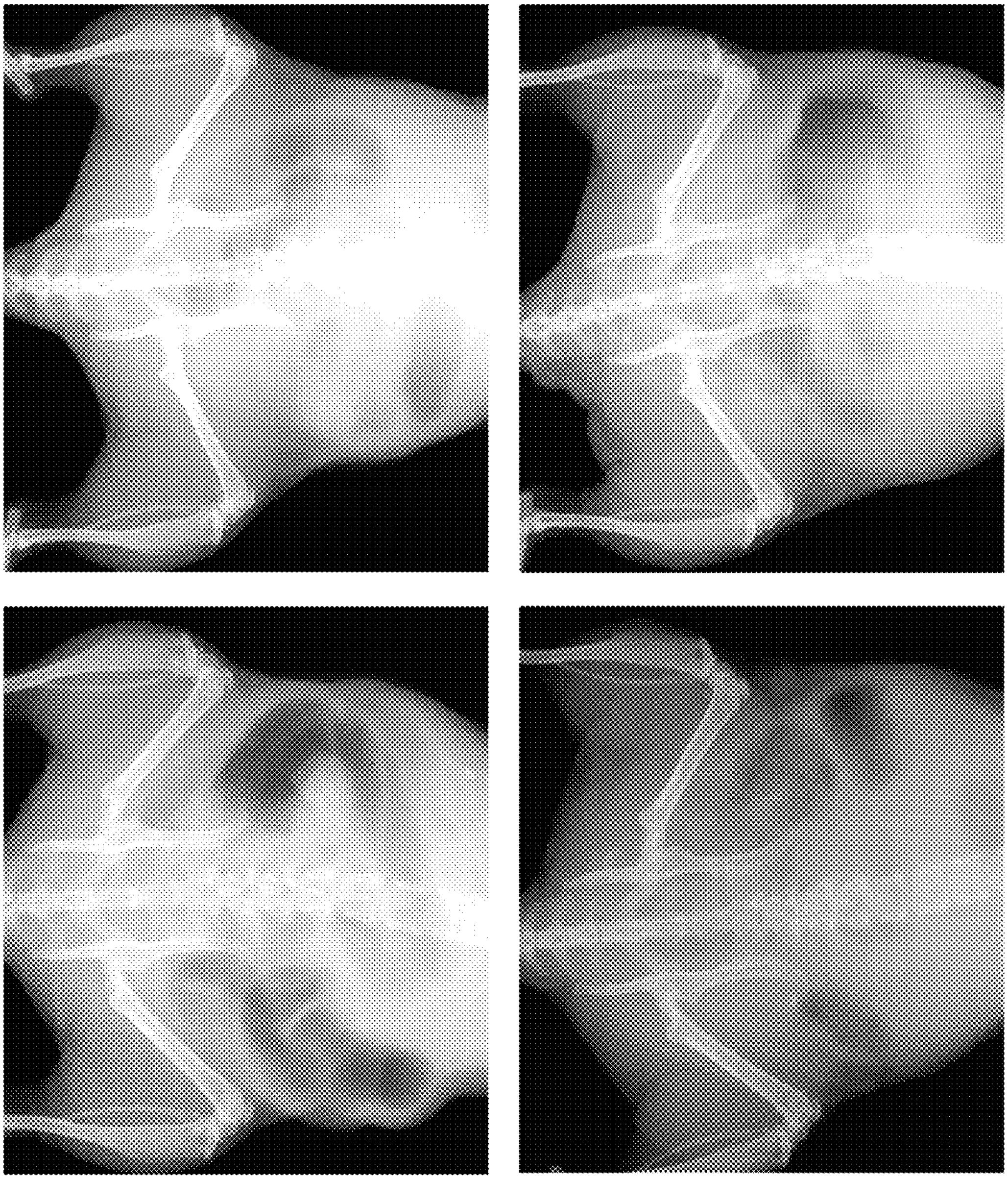
FIG. 4 shows radiographic appearance of intestinal air in Zibo+Castr group. Radiographs of four separate mice at various ages demonstrating excessive intestinal air.

However, the lack of significant weight gain was more evident in the Zibo+Castr group. Within 2-4 weeks of treatment initiation, mice in the Zibo+Castr group developed abdominal distension. Radiographic images of this group demonstrated intestinal gas distension within the stomach and intestines (FIG. 4). Two of the mice in this group lost more than 15% of weight and were euthanized at 34 and 42 days post-inoculation according to the pre-defined humane endpoints. However, no tumor was discovered at dissection or at survey of the skeleton by histology. As such, these two mice were removed from subsequent analyses. Due to concerns regarding undue potential selective side effects of zibotentan in castrated animals, the zibotentan dosing schedule was reduced in all treatment groups from seven to five days/week starting at day 59 post-inoculation. It was later concluded that the effects on the gastrointestinal tract were related to a side effect of zibotentan that resulted in immune-related damage of nasal olfactory epithelium leading to aerophagia and intestinal distention, as reported by our group.

Figures 5A, 5B:
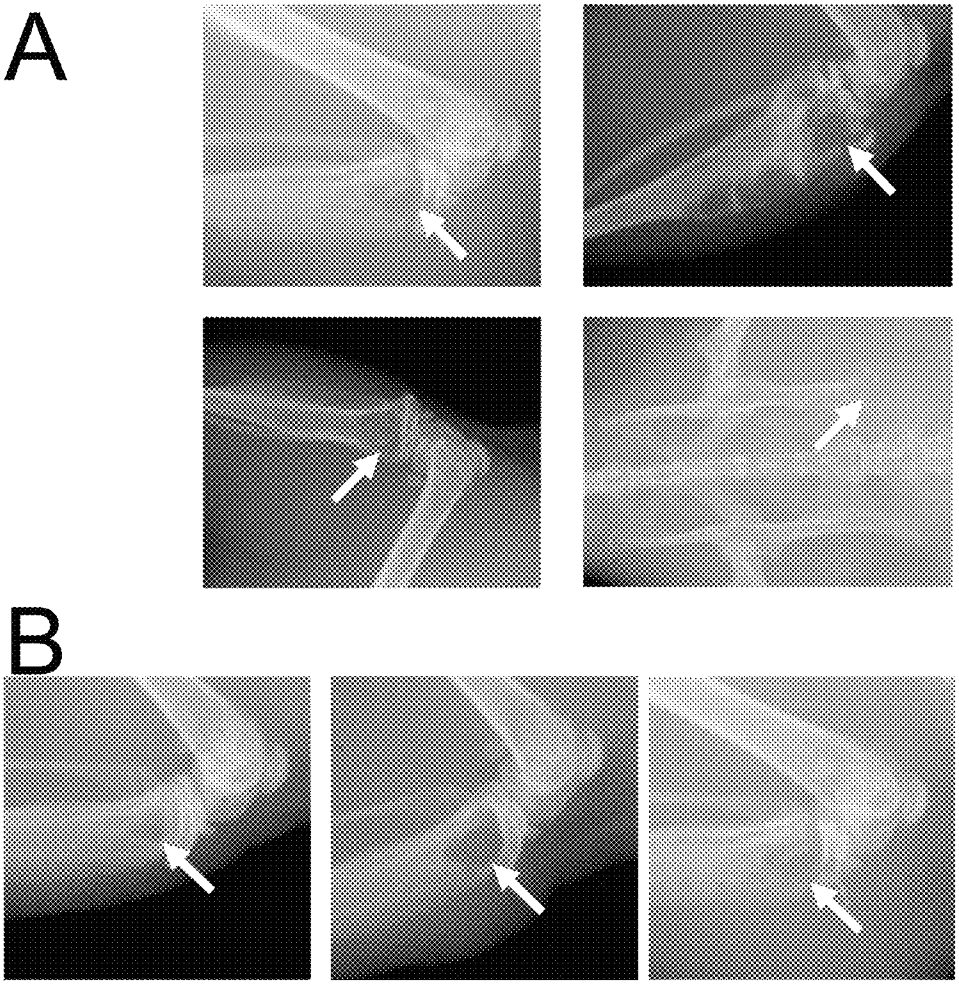
FIGS. 5A and 5B show examples of radiographic changes of $ARCaP_M$ skeletal lesions. (A) Examples of radiographic lesions in three tibiae and pelvis. (B) Progression of a tibial lesion over time.
Figure 6:
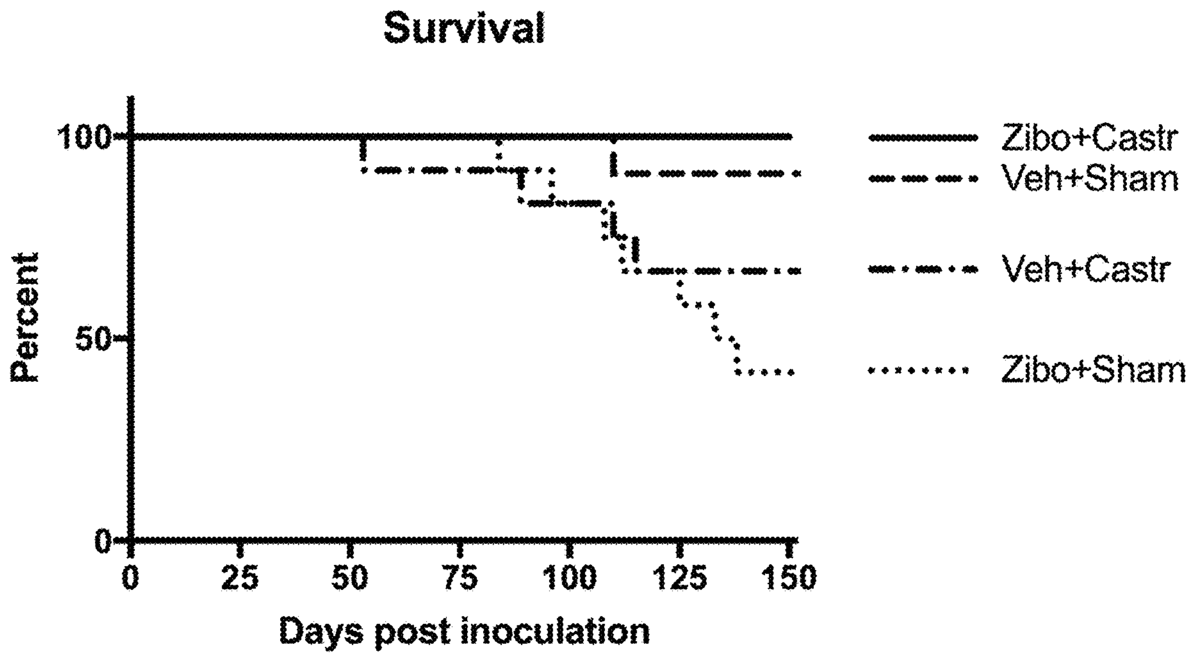
FIG. 6 shows Kaplan-Meier estimator survival plots. Statistical data was analyzed using the Kaplan-Meier method and Mantel-Cox statistical testing. Veh=vehicle control; Zibo=zibotentan; Sham=sham surgery; Castr=castration

The first radiographically evident bone lesion was detected at 45 days post-inoculation in a Veh+Castr animal. Similar lesions were subsequently discovered and were followed radiographically until the completion of the experiment (FIG. 5). Although the $ARCaP_M$ prostate cancer cells generate mixed osteosclerotic/osteolytic skeletal lesions, osteolytic lesions are radiographically apparent earlier. The experiment was terminated at day 152. Surviving animals were euthanized and tissues collected. No mouse in the Zibo+Castr group had detectable tumor at the completion of the experiment. Mice in the Zibo+Sham group had significantly shorter survival (p=0.0045). The restoration of ET-1 signaling in the Veh+Sham group resulted in significantly improved survival (p=0.0171). The remaining experimental group, Veh+Castr, had lower survival compared to Zibo+Castr (p=0.0050), indicating that in the absence of androgen signals, ET-1/$ET_A$R signaling supports prostate cancer growth in bone (FIG. 6).

4. Serum ET-1 Measurements

Figure 7:
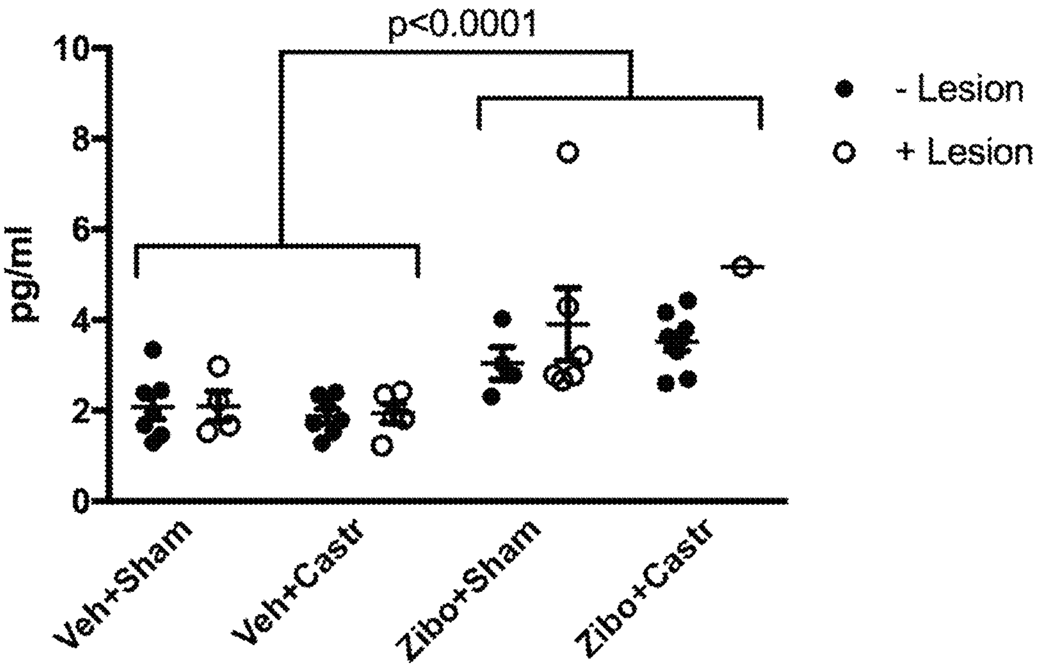
FIG. 7 shows changes in ET-1 concentration in serum in the four treatment groups. Sera were collected at euthanasia and frozen. Thawed sera were analyzed for ET-1 concentration using ELISA in the four experimental groups and further subdivided into the presence or absence of prostate cancer lesions. Data was analyzed using two-way ANOVA. Treatment with zibotentan was a significant source of statistical variation.

At euthanasia, sera were collected for measurement of circulating ET-1 concentration (FIG. 7). Within the experimental groups, there was no difference in serum ET-1 concentration between tumor-bearing and tumor-free mice. However, there was a trend for higher serum ET-1 in the zibotentan-treated tumor-bearing mice. There was however a significant increase in serum ET-1 concentration between vehicle control and zibotentan-treated mice.

5. Histologic Analyses

Figure 8:
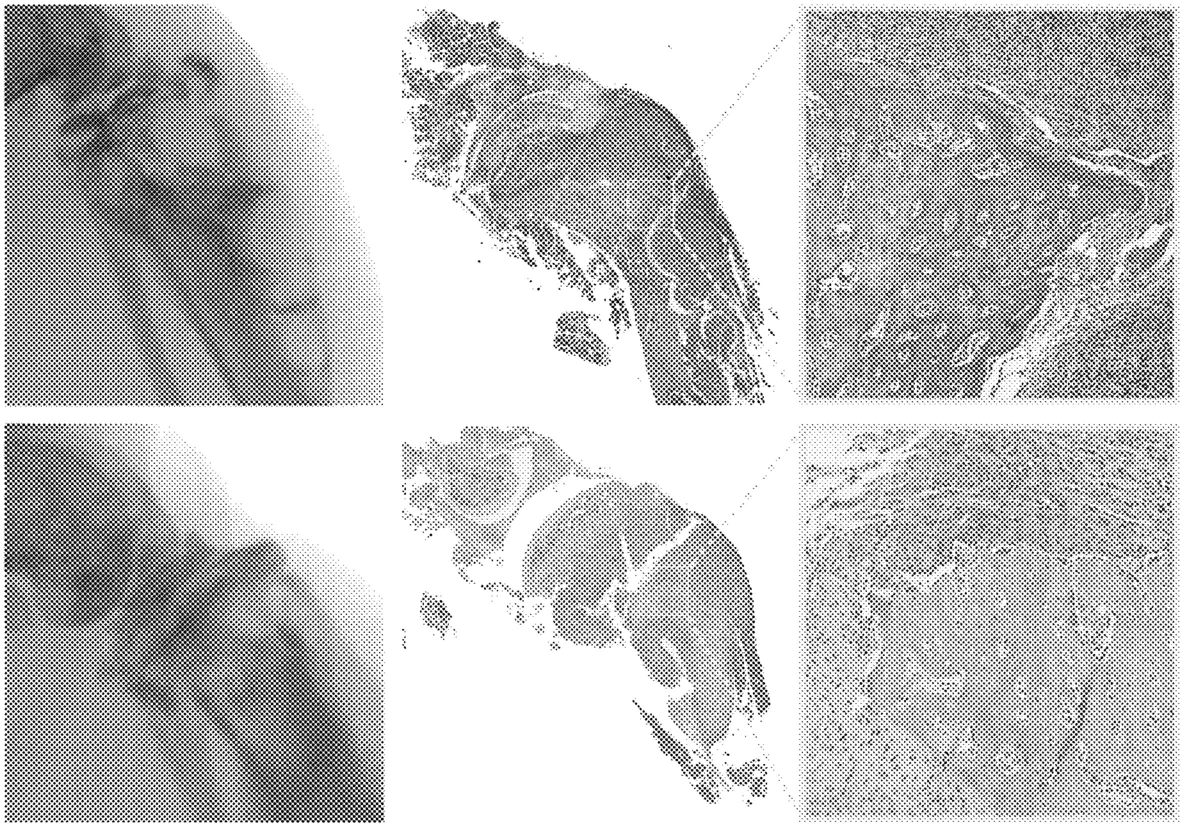
FIG. 8 shows examples of tibial skeletal lesions. Radiographic and histologic appearance of tibia lytic (arrows) and sclerotic (arrowheads) lesions. A magnified histologic view in last column demonstrates sclerotic pathologic bone (PB) and cancer cells (C). Histologic specimens were stained with H&E plus Orange G.

All long bones and spines were harvested, as well as other bones and soft tissues harboring lesions detected by radiography and/or discovered at dissection. Specimens were analyzed and surveyed for the presence of tumor cells by histology. Histologic analyses of skeletal lesions demonstrated the characteristic mixed osteosclerotic/lytic lesions of $ARCaP_M$ cells in bone. The cancer cells predominantly existed within lytic areas, and were adjacent to areas of increased bone formation and osteosclerosis (FIG. 8). One mechanism that drives the osteolytic response of the typical $ARCaP_M$ mixed osteosclerotic/osteoytic skeletal lesions is ET-1 from prostate cancer that promotes osteoblast secretion of osteoclast formation factors that include RANKL, IL-6 and IL-11.

Additional skeletal lesions were discovered in this survey that were not apparent by radiography or during visual inspection at dissection. This included an incidental small bone lesion from a single mouse in the Zibo+Castr group. Regarding the other groups, most lesions were located within the skeleton, but soft tissue tumors were also found. The occurrence of soft tissue tumors has been reported previously after systemic inoculation of $ARCaP_M$ cells. An unusual occurrence of ocular globe tumors was found, an uncommon site of metastasis in humans. The identity of these globe tumors was confirmed as human by immunohistochemistry using a human-specific antibody (data not shown). In total, 19 skeletal and 7 soft tissue tumors were discovered. The locations of these are reported in Table 1.

TABLE 1

Location and number of skeletal and soft tissue prostate cancer lesions.

Skeletal Lesions

| Region | Location | Veh + Sham | Veh + Castr | Zibo + Sham | Zibo + Castr | TOTAL |
|---|---|---|---|---|---|---|
| Right arm | Prox radius | | 1 | 1 | | 2 |
| | Prox humerus | | | 1 | | 1 |
| Left leg | Prox tibia | 2 | | 1 | 1 | 4 |
| | Dist femur | | | 1 | | 1 |
| Right leg | Prox tibia | 1 | 4 | | | 5 |
| Thoracic spine | T10 | | | 1 | | 1 |

TABLE 1-continued

Location and number of skeletal and soft tissue prostate cancer lesions.

| Region | Location | Veh + Sham | Veh + Castr | Zibo + Sham | Zibo + Castr | TOTAL |
|---|---|---|---|---|---|---|
| Xyphoid | | | 1 | | | 1 |
| Maxilla | | | | 2 | | 2 |
| Rib | | | | 1 | | 1 |
| Pelvis | R ilium | 1 | | | | 1 |
| TOTAL | | 4 | 6 | 8 | 1 | 19 |

Soft Tissue Lesions

| Location | Side | Veh + Sham | Veh + Castr | Zibo + Sham | Zibo + Castr | TOTAL |
|---|---|---|---|---|---|---|
| Eye | Left | | 1 | 1 | | 2 |
| | Right | 2 | 1 | | | 3 |
| Adrenal | Right | 1 | | 1 | | 2 |
| TOTAL | | 3 | 2 | 2 | 0 | 7 |

Figure 9A:
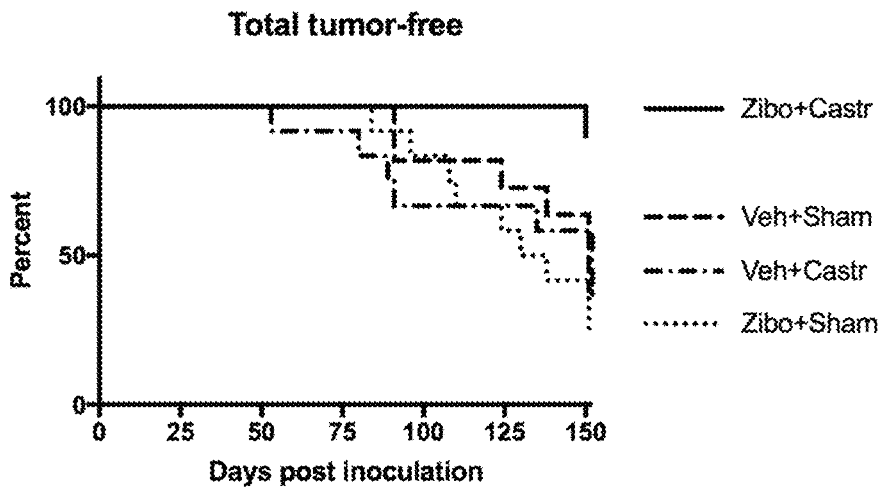
FIGS. 9A and 9B show Kaplan-Meier estimator plots demonstrating tumor-free status. Euthanasia, visual appearance of tumor, radiographic evidence of tumor, or the discovery of lesions at euthanasia determined the time in which an animal no longer remained tumor-free. The total tumor-free status was further divided into bone-specific tumor-free to delineate whether the tumor was first discovered in bone. Statistical data was analyzed using the Kaplan-Meier method and Mantel-Cox statistical testing. Veh=vehicle control; Zibo=zibotentan; Sham=sham surgery; Castr=castration
Figure 9B:
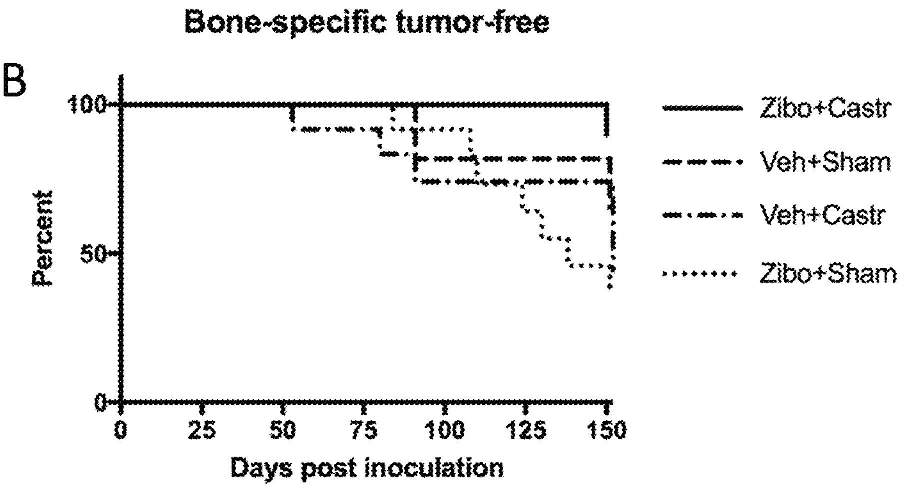

After $ARCaP_M$ lesion number and location were compiled, the primary outcome of the first tumor event was compared among the groups. A tumor event was defined as the day post-inoculation that a radiographic skeletal lesion was discovered. If a lesion was first discovered either at dissection or by histology, then the day of euthanasia was recorded as the tumor event. Kaplan-Meier analyses were performed assessing the time at which mice were no longer tumor-free. A single incidental skeletal lesion was discovered by histology in the Zibo+Castr group. As such, mice in this group had a significantly longer time to a tumor event than in the Zibo+Sham group (p=0.0149) (FIG. 9A). A secondary analysis was performed examining skeletal lesions only. The time to bone-specific tumor events was also longer in the Zibo+Castr compared to the Zibo+Sham group (p=0.0250) (FIG. 9B).

Figures 10A, 10B:
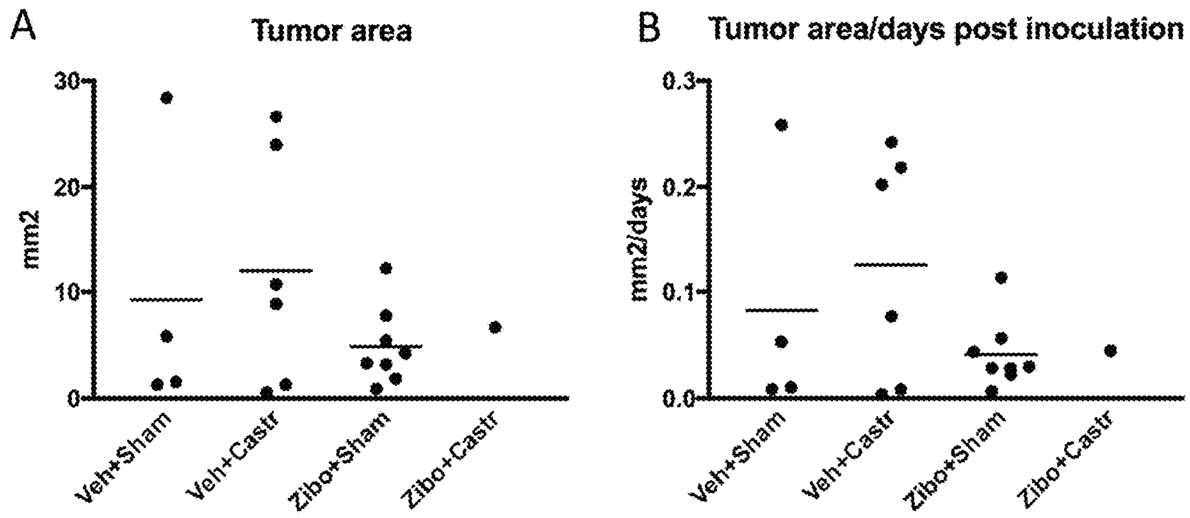
FIGS. 10A and 10B show the size of skeletal tumors as measured by histology. The bones from legs, spines and arms were collected at euthanasia, fixed, paraffin embedded and stained. The area of individual skeletal lesions was measured by histomorphometry (A). To account for the potential of skeletal lesions to increase in size with age, tumor size was adjusted to the age of the mouse at euthanasia (B). No significant differences were found between the size of tumors among the four treatment groups. Statistical data was analyzed using one-way ANOVA and Tukey's multiple comparison testing. Veh=vehicle control; Zibo=zibotentan; Sham=sham surgery; Castr=castration

Skeletal histomorphometric analyses were performed to determine skeletal lesion area among the treatment groups. No significant differences were detected among the Veh+Sham, Veh+Castr, and Zibo+Sham groups (FIG. 10A). The Zibo+Castr group was not included in the analyses due to the presence of a single value. To account for the potential of lesions to grow larger in older mice, tumor area was adjusted to the day post-inoculation of euthanasia. Likewise, differences among the groups were not detected (FIG. 10B).

H. Discussion

Prostate cancer metastatic to bone secretes factors such as ET-1 that alter the bone microenvironment. Osteoblasts in turn secrete prostate cancer growth factors solidifying a crosstalk-signaling network. Despite the apparent importance of ET-1 in prostate cancer progression, the results of $ET_A$R antagonist clinical trials were largely disappointing. Criticisms of these clinical trials have included choosing overall survival and disease progression as primary outcomes despite pre-clinical animal data demonstrating that ET-1/$ET_A$R signaling axis governs bone-specific metastasis, not tumor growth outside of bone.

Another limitation of the $ET_A$R antagonist clinical trials was the lack of complete androgen deprivation. Standard ADT, that includes surgical castration and gonadotropin-releasing hormone (GnRH) agonists/antagonists, targets only testicular production of androgen. Adrenal androgens and even prostate cancer production of androgens remain constant sources of prostate cancer stimulation. Medications currently available that effectively block androgen synthesis (abiraterone acetate) and androgen action at the receptor level (enzalutamide) were not yet approved at the time of the atrasentan and zibotentan clinical trials. We now propose a potential reason for the failure of these trials.

The study reported here was designed to determine how the combination of $ET_AR$ blockade combined with castration affected the development of skeletal lesions and survival in a mouse model of prostate cancer bone metastasis. One advantage of a mouse model of prostate cancer is that castration of male mice results in complete androgen deprivation. Unlike humans, mice do not synthesize adrenal androgens and therefore lack adrenal androgen precursors that fuel prostate cancer intratumoral generation of active androgens. The design of the experiments was based on a model in which prostate cancer ET-1 secretion stimulates osteoblast-dependent new bone formation. The use of a castrate-resistant or repressed cell line is also a critical aspect to replicate the advanced stage of disease in human CRPC metastasis. The $ARCaP_M$ prostate cancer cell line represented the ideal model since it secretes ET-1, is castrate-resistant, and forms bone lesions in mice after intracardiac inoculation.

At euthanasia, sera were collected for circulating ET-1 measurements. ET-1 concentrations were similar between tumor-bearing and tumor-free mice. This is in contrast to men with advanced prostate cancer with metastatic disease whereby circulating ET-1 is higher compared to men without metastasis 3. The likely reason for the lack of difference in the animal model is that tumor burden was unlikely great enough to exceed that of existing vascular endothelial-derived ET-1, the principal source of circulating ET-1. ET-1 concentrations however were higher in zibotentan-treated mice and a likely consequence of a compensatory increase in ligand with receptor blockade.

As expected, castration in vehicle-treated groups (Veh+Castr vs. Veh+Sham) did not change the development of skeletal lesions or survival since $ARCaP_M$ cells are castrate-resistant. However, castration reduced the number of skeletal lesions and increased survival in zibotentan treated groups (Zibo+Castr vs. Zibo+Sham). In fact, a single incidental skeletal lesion was found in the Zibo+Castr group. These data indicate that $ET_AR$ blockade can sensitize prostate cancer skeletal lesions to the effects of androgen. If so, then one would predict that $ET_AR$ blockade might actually worsen skeletal lesions in sham-operated mice where androgen is present. Zibotentan did in fact decrease survival in sham-operated mice (Zibo+Sham vs. Veh+Sham). But in the absence of androgen, zibotentan not only improved survival (Zibo+Castr vs. Veh+Castr) but also resulted in the lack of radiographically apparent lesions at the end the experiment at 152 days. There was no survival difference between the Zibo+Castr and Veh+Sham groups. However, there were more lesions and a trend for fewer tumor-free days in the Veh+Sham group. It was unclear why animals receiving no treatment were able to survival longer with more lesions. This may be related to other factors such as the production of inflammatory cytokines and thus affecting the likelihood of mice meeting humane endpoints for euthanasia.

Figure 11:
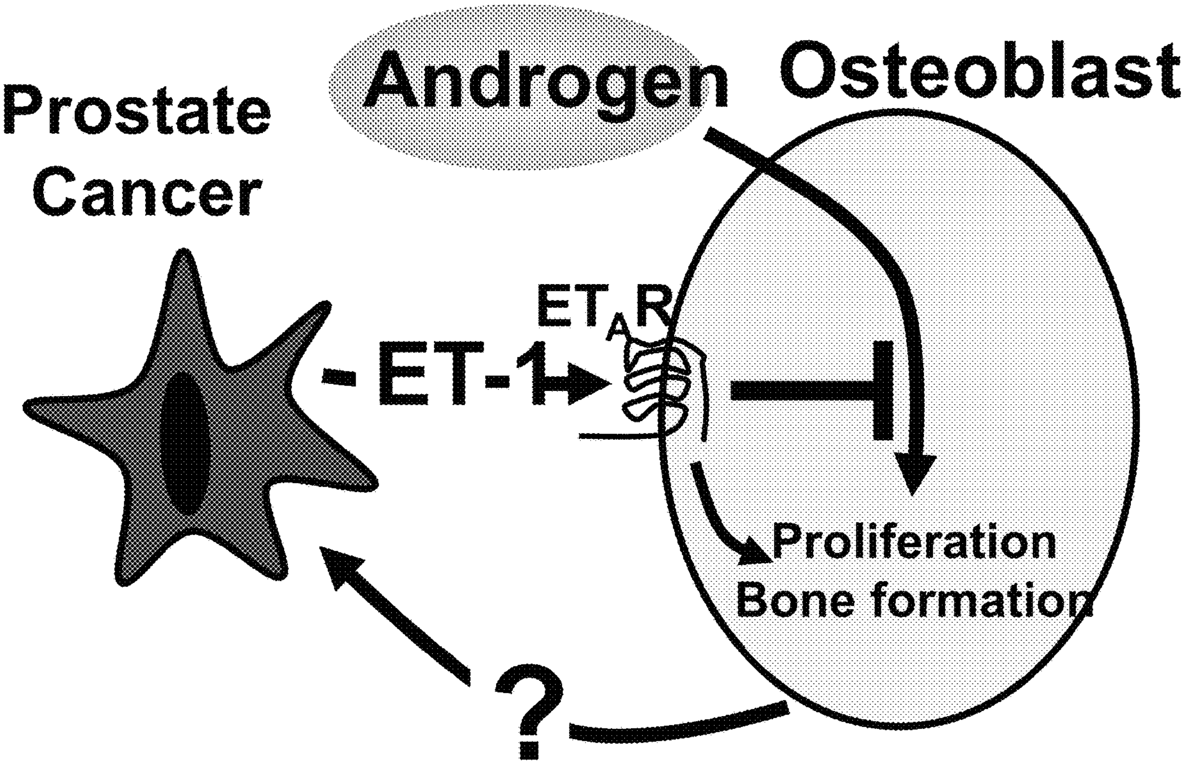
FIG. 11 shows a model of osteoblast ET-1/$ET_AR$ and androgen signaling interaction. ET-1 secreted by prostate cancer cells increases osteoblast proliferation and new bone formation. ET-1/$ET_AR$ signaling also limits androgen action in the osteoblast. Osteoblasts respond to androgen and ET-1 interacting signals through expression of prostate cancer growth factors.

These data may be explained by a model in which $ET_AR$ blockade sensitizes the osteoblast to androgen and therefore unleashes the effects of androgen to drive expression of osteoblast-derived prostate cancer growth factors (FIG. 11). This model is supported by data reporting an interaction between ET-1/$ET_AR$ and androgen signaling during bone remodeling of adult male mice. In this report, osteoblast-specific $ET_AR$ inactivation caused reduced bone accrual in male castrated mice, but increased bone accrual in eugonadal male mice. These data indicate that while both ET-1 and androgen promote bone formation, ET-1 can also limit the known anabolic effects of androgen on the osteoblast. A picture of how endothelin and androgen signaling converge is not clear but can involve reported interactions between Wnt and androgen signaling. Thus, complete androgen deprivation is required to minimize prostate cancer growth when combined with $ET_AR$ blockade.

The combination of zibotentan and castration had unintended consequences that included weight loss, diffuse gas distention within the stomach and intestines, and respiratory epithelial inflammation. These findings indicate that ET-1/$ET_AR$ and androgen signaling cooperate outside of the skeleton. While the upper airway irritation was not surprising, especially since this is a common side effect of $ET_AR$ antagonists in clinical use, it was unexpected that this was found only in the castration group. This can indicate that androgens have important actions in the upper airway. The intestinal gas was likely due to aerophagia as a consequence of the changes in the nasal cavity. The extent to which other tissues are affected by the combination $ET_AR$ blockade and androgen depletion is unclear and uninvestigated.

A limitation of this study is the use of a human prostate cancer xenograft cell line rather than a syngeneic mouse prostate cancer cell line. Unfortunately, mouse prostate cancer cell lines, that include TRAMP-C1, infrequently form skeletal lesions after inoculation 32,41,42 Numerous transgenic mouse lines have been developed that spontaneously form prostate cancer but infrequently, if ever, form skeletal lesions[43]. The research field therefore relies on xenograft cell inoculation into immunodeficient mice. The contribution of immune cells to prostate cancer skeletal lesions is becoming more recognized and is often a neglected aspect in mouse models of prostate cancer bone metastasis[44]. Despite these limitations, the $ARCaP_M$ model of prostate cancer bone metastasis chosen because of key characteristics replicated in human disease that include castrate-resistance, formation of mixed osteosclerotic/osteolytic skeletal lesions after inoculation, and significant ET-1 expression. Another limitation of this study was the reliance of a single prostate cancer cell line. Numerous human prostate cancer cell lines and xenografts have been developed. While there are advantages and disadvantages to each one, no one model has stood out as being ideal. An important future study would be test the interaction of endothelin and androgen signaling in another prostate cancer bone metastasis model.

The data presented here support a mechanism of ET-1/$ET_AR$ control of androgen signaling. It is unclear the extent to which other androgen-responsive tissues may also be regulated by ET-1/$ET_AR$ signaling. More importantly, these data have significant implications for men treated for advanced prostate cancer. $ET_AR$ antagonists have had mixed results regarding reduced skeletal burden in men with advanced prostate cancer. Continued ADT is standard of care in men with advanced prostate cancer despite the lack of evidence that it reduces tumor burden, osteoblastic lesions or mortality. Controversy continues on whether ADT should be continued in men with castrate-resistant prostate cancer. The data indicate that $ET_AR$ blockade, intended to reduce the osteosclerotic response to prostate cancer, can have little effect in the presence of androgen. Thus, complete androgen deprivation using modern agents such as abiraterone acetate and enzalutamide, rather than standard ADT can be required to minimize prostate cancer growth when combined with $ET_AR$ blockade.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Bubendorf L, Schopfer A, Wagner U, et al. Metastatic patterns of prostate cancer: an autopsy study of 1,589 patients. *Hum Pathol.* 2000; 31(5):578-583.
2. Weilbaecher K N, Guise T A, McCauley L K. Cancer to bone: a fatal attraction. *Nat Rev Cancer.* 2011; 11(6):411-425.
3. Nelson J B, Hedican S P, George D J, et al. Identification of endothelin-1 in the pathophysiology of metastatic adenocarcinoma of the prostate. *Nature Medicine.* 1995; 1 (9):944-949.
4. Yanagisawa M, Kurihara H, Kimura S, et al. A novel potent vasoconstrictor peptide produced by vascular endothelial cells. *Nature.* 1988; 332(6163):411-415.
5. Nelson J B, Nabulsi A A, Vogelzang N J, et al. Suppression of prostate cancer induced bone remodeling by the endothelin receptor A antagonist atrasentan. *Journal of Urology.* 2003; 169(3):1143-1149.
6. Yin J J, Mohammad K S, Kakonen S M, et al. A causal role for endothelin-1 in the pathogenesis of osteoblastic bone metastases. *Proceedings of the National Academy of Sciences of the United States of America.* 2003; 100 (19):10954-10959.
7. Clines G A, Mohammad K S, Bao Y, et al. Dickkopf homolog 1 mediates endothelin-1-stimulated new bone formation. *Molecular Endocrinology.* 2007; 22:486-498.
8. Little R D, Carulli J P, Del Mastro R G, et al. A mutation in the LDL receptor-related protein 5 gene results in the autosomal dominant high-bone-mass trait. *American Journal of Human Genetics.* 2002; 70(1):11-19.
9. Boyden L M, Mao J, Belsky J, et al. High bone density due to a mutation in LDL-receptor-related protein 5. *New England Journal of Medicine.* 2002; 346(20):1513-1521.
10. Gong Y, Slee R B, Fukai N, et al. LDL receptor-related protein 5 (LRP5) affects bone accrual and eye development. *Cell.* 2001; 107(4):513-523.
11. Holmen S L, Giambernardi T A, Zylstra C R, et al. Decreased BMD and Limb Deformities in Mice Carrying Mutations in Both Lrp5 and Lrp6. *Journal of Bone & Mineral Research.* 2004; 19(12):2033-2040.
12. Drake J M, Danke J R, Henry M D. Bone-specific growth inhibition of prostate cancer metastasis by atrasentan. *Cancer Biol Ther.* 2010; 9(8):607-614.
13. Carducci M A, Padley R J, Breul J, et al. Effect of endothelin-A receptor blockade with atrasentan on tumor progression in men with hormone-refractory prostate cancer: a randomized, phase II, placebo-controlled trial. *Journal of Clinical Oncology.* 2003; 21(4):679-689.
14. Carducci M A, Saad F, Abrahamsson P A, et al. A phase 3 randomized controlled trial of the efficacy and safety of atrasentan in men with metastatic hormone-refractory prostate cancer. *Cancer.* 2007; 110(9):1959-1966.
15. Quinn D I, Tangen C M, Hussain M, et al. Docetaxel and atrasentan versus docetaxel and placebo for men with advanced castration-resistant prostate cancer (SWOG S0421): a randomised phase 3 trial. *Lancet Oncol.* 2013; 14(9):893-900.
16. Lara P N, Jr., Ely B, Quinn D I, et al. Serum biomarkers of bone metabolism in castration-resistant prostate cancer patients with skeletal metastases: results from SWOG 0421. *J Natl Cancer Inst.* 2014; 106(4):dju013.
17. James N D, Caty A, Borre M, et al. Safety and efficacy of the specific endothelin-A receptor antagonist ZD4054 in patients with hormone-resistant prostate cancer and bone metastases who were pain free or mildly symptomatic: a double-blind, placebo-controlled, randomised, phase 2 trial. *Eur Urol.* 2009; 55(5):1112-1123.
18. Nelson J B, Fizazi K, Miller K, et al. Phase 3, randomized, placebo-controlled study of zibotentan (ZD4054) in patients with castration-resistant prostate cancer metastatic to bone. *Cancer.* 2012.
19. Clines G A, Mohammad K S, Grunda J M, et al. Regulation of postnatal trabecular bone formation by the osteoblast endothelin A receptor. *Journal of Bone and Mineral Research.* 2011; 26(10):2523-2536.
20. Klein H, Bressel M, Kastendieck H, Voigt K D. Androgens, adrenal androgen precursors, and their metabolism in untreated primary tumors and lymph node metastases of human prostatic cancer. *Am J Clin Oncol.* 1988; 11 Suppl 2:S30-36.
21. Dillard P R, Lin M F, Khan S A. Androgen-independent prostate cancer cells acquire the complete steroidogenic potential of synthesizing testosterone from cholesterol. *Mol Cell Endocrinol.* 2008; 295(1-2):115-120.
22. Stuchbery R, McCoy P J, Hovens C M, Corcoran N M. Androgen synthesis in prostate cancer: do all roads lead to Rome? Nat *Rev Urol.* 2017; 14(1):49-58.
23. van Weerden W M, Bierings H G, van Steenbrugge G J, de Jong F H, Schroder F H. Adrenal glands of mouse and rat do not synthesize androgens. *Life Sci.* 1992; 50(12):857-861.
24. Sedelaar J P M, Dalrymple S S, Isaacs J T. Of mice and men-warning: Intact versus castrated adult male mice as xenograft hosts are equivalent to hypogonadal versus abiraterone treated aging human males, respectively. *The Prostate.* 2013; 73:1316-1325.
25. Zhau H E, Li C L, Chung L W. Establishment of human prostate carcinoma skeletal metastasis models. *Cancer.* 2000; 88(12 Suppl):2995-3001.
26. Xu J, Wang R, Xie Z H, et al. Prostate cancer metastasis: role of the host microenvironment in promoting epithelial to mesenchymal transition and increased bone and adrenal gland metastasis. *Prostate.* 2006; 66(15):1664-1673.
27. Guise T A, Yin J J, Taylor S D, et al. Evidence for a causal role of parathyroid hormone-related protein in the pathogenesis of human breast cancer-mediated osteolysis. *Journal of Clinical Investigation.* 1996; 98(7):1544-1549.
28. Morris C D, Rose A, Curwen J, Hughes A M, Wilson D J, Webb D J. Specific inhibition of the endothelin A receptor with ZD4054: clinical and pre-clinical evidence. *Br J Cancer.* 2005; 92(12):2148-2152.
29. Rosano L, Di Castro V, Spinella F, Nicotra M R, Natali P G, Bagnato A. ZD4054, a specific antagonist of the endothelin A receptor, inhibits tumor growth and enhances paclitaxel activity in human ovarian carcinoma in vitro and in vivo. *Mol Cancer Ther.* 2007; 6(7):2003-2011.
30. Growcott J W. Preclinical anticancer activity of the specific endothelin A receptor antagonist ZD4054. *Anti-cancer Drugs.* 2009; 20(2):83-88.
31. Haque S U, Dashwood M R, Heetun M, et al. Efficacy of the specific endothelin a receptor antagonist zibotentan (ZD4054) in colorectal cancer: a preclinical study. *Mol Cancer Ther.* 2013; 12(8):1556-1567.
32. Dai J, Hensel J, Wang N, Kruithof-de Julio M, Shiozawa Y. Mouse models for studying prostate cancer bone metastasis. *Bonekey Rep.* 2016; 5:777.
33. Grunda J M, Wang D, Clines G A. Development and characterization of murine models of medulloblastoma extraneural growth in bone. *Clin Exp Metastasis.* 2013; 30(6):769-779.
34. Hewitson T D, Zhao C, Wigg B, et al. Relaxin and castration in male mice protect from, but testosterone exacerbates, age-related cardiac and renal fibrosis, whereas estrogens are an independent determinant of organ size. *Endocrinology.* 2012; 153(1):188-199.
35. Zhang X, Thatcher S, Wu C, Daugherty A, Cassis L A. Castration of male mice prevents the progression of established angiotensin I I-induced abdominal aortic aneurysms. *J Vasc Surg.* 2015; 61(3):767-776.
36. Esvelt M A, Freeman Z T, Pearson A T, et al. The Endothelin-A Receptor Antagonist Zibotentan Induces Damage to the Nasal Olfactory Epithelium Possibly Mediated in Part through Type 2 Innate Lymphoid Cells. *Toxicol Pathol.* 2018:192623318816295.
37. Yang F, Li X, Sharma M, et al. Linking beta-catenin to androgen-signaling pathway. *J Biol Chem.* 2002; 277(13): 11336-11344.
38. Singh R, Bhasin S, Braga M, et al. Regulation of myogenic differentiation by androgens: cross talk between androgen receptor/beta-catenin and follistatin/transforming growth factor-beta signaling pathways. *Endocrinology.* 2009; 150(3):1259-1268.
39. Liu X H, Kirschenbaum A, Yao S, Liu G, Aaronson S A, Levine A C. Androgen-induced Wnt signaling in preosteoblasts promotes the growth of MDA-PCa-2b human prostate cancer cells. *Cancer Res.* 2007; 67(12):5747-5753.
40. Wei A, Gu Z, Li J, et al. *Clinical Adverse Effects of Endothelin Receptor* Antagonists: Insights From the Meta-Analysis of 4894 Patients From 24 Randomized Double-Blind Placebo-Controlled Clinical Trials. *J Am Heart Assoc.* 2016; 5(11).
41. Rosol T J, Tannehill-Gregg S H, LeRoy B E, Mandl S, Contag C H. Animal models of bone metastasis. *Cancer.* 2003; 97(3 Suppl):748-757.
42. Gelman I H. How the TRAMP Model Revolutionized the Study of Prostate Cancer Progression. *Cancer Res.* 2016; 76(21):6137-6139.
43. Simmons J K, Hildreth B E, 3rd, Supsavhad W, et al. Animal Models of Bone Metastasis. *Vet Pathol.* 2015; 52(5):827-841.
44. Xiang L, Gilkes D M. The Contribution of the Immune System in Bone Metastasis Pathogenesis. *Int J Mol Sci.* 2019; 20(4).
45. Smith M R, Lee W C, Brandman J, Wang Q, Botteman M, Pashos C L. Gonadotropin-releasing hormone agonists and fracture risk: a claims-based cohort study of men with nonmetastatic prostate cancer. *Journal of Clinical Oncology.* 2005; 23(31):7897-7903.

I claim:

1. A method of preventing prostate cancer metastasis to bone comprising administering to a subject having prostate cancer an ETAR antagonist, an anti-androgen therapy, and castration therapy, wherein the $ET_AR$ antagonist is zibotentan or atrasentan, wherein the anti-androgen therapy is abiraterone acetate, enzalutamide, apalutamide, or darolutamide, and wherein the castration therapy is chemical castration or physical castration.

2. The method of claim 1, wherein the subject has advanced prostate cancer or castrate-resistant prostate cancer (CRPC).

3. The method of claim 1, wherein the ETAR antagonist and the anti-androgen therapy are administered simultaneously.

4. The method of claim 1, wherein the ETAR antagonist and the anti-androgen therapy are administered in separate formulations.

5. The method of claim 1, wherein the ETAR antagonist is also an endothelin-1 (ET-1) antagonist.

* * * * *